United States Patent [19]
Kokubo et al.

[11] Patent Number: 5,776,501
[45] Date of Patent: Jul. 7, 1998

[54] COATING BASE FOR SOLID ENTERIC PHARMACEUTICAL PREPARATIONS

[75] Inventors: Hiroyasu Kokubo; Takashi Tanaka, both of Niigata, Japan

[73] Assignee: Shin-Etsu Chemical Co., Ltd., Tokyo, Japan

[21] Appl. No.: 554,834

[22] Filed: Nov. 7, 1995

[30] Foreign Application Priority Data

Nov. 7, 1994 [JP] Japan ................................. 6-272397

[51] Int. Cl.$^6$ ............................. A61K 9/32; C08B 11/00
[52] U.S. Cl. ..................... 424/494; 106/181.1; 424/480; 536/56; 536/89
[58] Field of Search ........................... 424/480, 490, 424/497, 494; 106/172.1, 162.7, 162.71, 162.72, 162.8, 163.01, 181.1; 536/56, 84, 85, 89, 90, 91, 95, 96, 99

[56] References Cited

U.S. PATENT DOCUMENTS

| | | | |
|---|---|---|---|
| 2,093,462 | 9/1937 | Malm et al. | 536/35 |
| 3,789,117 | 1/1974 | Tsujino | 424/480 |
| 3,816,150 | 6/1974 | Ishii et al. | 106/170.41 |
| 3,968,277 | 7/1976 | Takase | 427/212 |
| 4,661,162 | 4/1987 | Kurihara et al. | 106/169 |
| 5,540,945 | 7/1996 | Ikushima | 424/490 |

*Primary Examiner*—Robert H. Harrison
*Attorney, Agent, or Firm*—Sughrue, Mion, Zinn, Macpeak & Seas, PLLC

[57] ABSTRACT

The present invention provides a base for coating a solid enteric pharmaceutical preparation whose dissolution pH ranges from 3 to 4. The coating base is a cellulose acetate maleate which is prepared by substituting a water-soluble cellulose derivative with 0.25 to 0.5 acetyl group and 0.35 to 0.6 maleyl group per glucose ring of the cellulose derivative. The cellulose acetate maleate has a dissolution pH ranging from 3 to 4.

2 Claims, No Drawings

1

COATING BASE FOR SOLID ENTERIC PHARMACEUTICAL PREPARATIONS

BACKGROUND OF THE INVENTION

The present invention relates to a base for use in coating a solid enteric pharmaceutical preparation which is dissolved in the intestine and shows its pharmacological action.

The solid enteric pharmaceutical preparation is provided with an enteric coating film for the purposes of protecting drugs exhibiting low resistance to acids from the attack of the acid in the stomach, of protecting the gastric mucous membrane from the attack of drugs which may stimulate and damage the wall of the stomach and is dissolved after the arrival at the intestines in which the enteric pharmaceutical preparation shows its pharmacological action. As bases for use in coating the enteric pharmaceutical preparation, there have been known cellulosic polymers, vinyl polymers and acrylic polymers. Specifically, the cellulosic polymer may be, for instance, cellulose acetate phthalate, cellulose acetate trimellitate, hydroxypropylmethyl cellulose phthalate, hydroxypropylmethyl cellulose acetate succinate and carboxymethylethyl cellulose; the vinyl polymer may be, for instance, polyvinyl alcohol acetate phthalate; and the acrylic polymer may be, for instance, copolymers of methacrylic acid and ethyl acrylate.

A coating liquid is prepared by dissolving these coating bases in an organic solvent or dispersing them in a proper solvent to form an aqueous latex or an aqueous dispersion and then the liquid is applied to drugs. These coating bases can be dissolved at a pH ranging from 5 to 7. A solid enteric pharmaceutical preparation can be prepared by applying a coating liquid to a drug and then drying to form a film covering the drug.

The pharmacological action of a solid enteric pharmaceutical preparation is greatly affected by the solubility of such a film covering the drug included in the preparation. More specifically, unless the film is dissolved to some extent to initiate the release of the drug before the enteric pharmaceutical preparation arrive at the small intestine, the preparation passes through the small intestine before the preparation completely releases the drug included therein. For this reason, there has long been investigated the solubility of the enteric polymer as a principal component of the film.

Remington's Pharmaceutical Sciences, 13th ed., p. 604, published by Mack Publishing Co. (1965) discloses that the enteric polymer carries carboxyl groups and hydrophobic groups in the molecule and the enteric polymer is dissolved in a solvent having a specific pH value through the dissociation of the carboxyl groups thereof. For instance, commercially available hydroxypropylmethyl cellulose acetate succinate is a derivative of hydroxypropylmethyl cellulose which is substituted with carboxyl groups (succinoyl groups) and hydrophobic groups (acetyl groups). The solubility of hydroxypropylmethyl cellulose acetate succinate can be controlled by variously changing the degrees of substitution with succinoyl groups and acetyl groups. In addition, Aqueous Polymeric Coatings for Pharmaceutical Dosage Forms, T. Nagai et al., Chapter 3, p. 108, published by Marcel Dekker, Inc. (1989) discloses that hydroxypropylmethyl cellulose acetate succinate is soluble in an aqueous solvent at a pH ranging from 5 to 7.

U.S. Pat. No. 2,093,462 discloses that cellulose acetate succinate and cellulose acetate maleate are soluble in an aqueous solvent at a pH ranging from 5 to 6.5 and the solubility characteristics thereof are identical to those observed for cellulose acetate phthalate.

Moreover, Japanese Patent Application Publication No. 48-19391 discloses that if cellulose acetate is substituted with a dibasic carboxylic acid (phthalic acid) to give cellulose acetate phthalate, the resulting cellulose acetate phthalate is soluble in an aqueous solvent at a pH of 5.5, while if cellulose acetate is substituted with trimellitic acid which is a tribasic acid and has a high degree of dissociation and low hydrophobicity to give cellulose acetate trimellitate, the resulting cellulose acetate trimellitate is soluble therein at a pH of 5.0. The patent further discloses that if hydroxypropylmethyl cellulose is substituted with trimellitic acid to form hydroxypropylmethyl cellulose trimellitate, the resulting hydroxypropylmethyl cellulose trimellitate is soluble at a pH of 4.5.

L. C. Lappas, W. Mckeehan, J. Pharm. Sci., 54, 176 (1965) discloses that a vinyl methyl ether-maleic acid copolymer is soluble in water, the solubility of the copolymer can be controlled by changing the size (or bulkiness) of the alkyl group on the copolymer molecule and the copolymer accordingly has a dissolution pH ranging from 4.1 to 8.

As has been discussed above, there have been known a plurality of means for improving the solubility of the enteric polymer which serves as the base for coating the solid enteric pharmaceutical preparation. However, the foregoing improvement in the solubility is not still satisfied and accordingly, the preparation often passes through the upper portion of the small intestine before the preparation completely releases the drug included therein and does not sufficiently show its pharmacological action. In order to allow the enteric pharmaceutical preparation to show its pharmacological action, it is necessary to develop a coating base having a dissolution pH of not more than 4 and to thus further improve the solubility of the coating film of the solid enteric pharmaceutical preparation.

SUMMARY OF THE INVENTION

The present invention has been developed to solve the foregoing problems associated with the conventional techniques and accordingly, it is an object of the present invention to provide a coating base for a solid enteric pharmaceutical preparation, whose dissolution pH ranges from 3 to 4.

The base for coating a solid enteric pharmaceutical preparation which has been developed for accomplishing the foregoing object of the present invention is a cellulose acetate maleate which is obtained by substituting a water-soluble cellulose derivative with 0.25 to 0.5 acetyl group and 0.35 to 0.6 maleyl group per glucose ring of the cellulose derivative and which has a dissolution pH ranging from 3 to 4.

DETAILED EXPLANATION OF THE INVENTION

The present invention will hereinafter be described in more detail.

The water-soluble cellulose derivative usable herein may be, for instance, methyl cellulose, hydroxypropylmethyl cellulose, hydroxypropyl cellulose and hydroxyethyl cellulose, with hydroxypropylmethyl cellulose being particularly preferred because of its high solubility in an organic solvent and high strength of the resulting coating film.

The water-soluble cellulose derivative preferably has a viscosity (as determined using a 2% by weight aqueous solution thereof) ranging from 3 to 10 cP. This is because if the viscosity is less than 3 cP, the finally obtained coating film for solid enteric pharmaceutical preparations is insufficient in the strength, while if it exceeds 10 cP, the viscosity observed when it is dissolved in a solvent to carry out a substitution reaction becomes extremely high.

The solubility of the cellulose acetate maleate as the reaction product is greatly affected by the numbers of acetyl groups and maleyl groups (numbers of substituted groups) with which the water-soluble cellulose derivative is substituted. The number of the substituted acetyl groups suitably ranges from 0.2 to 0.5 per glucose ring of the water-soluble cellulose derivative. This is because if it is less than 0.2, the resulting coating base is insufficient in the hydrophobicity because of a low content of hydrophobic acetyl groups and the resulting base is, in turn, insufficient in resistance to acids. On the other hand, if it is more than 0.5, the hydrophobicity of the resulting cellulose acetate maleate is extremely high and accordingly, the dissolution pH thereof is higher than 4.

The number of the substituted maleyl groups suitably ranges from 0.35 to 0.6. If the number of the substituted maleyl groups is less than 0.35, the dissolution of the resulting cellulose acetate maleate through the dissociation of the maleyl groups is insufficient and the dissolution pH thereof is higher than 4. On the other hand, if it exceeds 0.6, the dissolution pH of the resulting acetate maleate is less than 3 and accordingly, the acetate maleate does not exhibit resistance to acids sufficient for use as a coating base. Moreover, a large amount of the acetate maleate is dissolved in water during crystallization and washing processes and this makes the washing thereof difficult.

The cellulose acetate maleate of the present invention has a dissolution pH ranging from 3 to 4. The dissolution pH is determined according to the following method. More specifically, the cellulose acetate maleate as a coating base is dissolved in an organic solvent to form a coating solution and the coating solution is casted into a film having a thickness of 100 μm on a glass plate. Then the film is cut into pieces each having a size of 1 cm×1 cm, followed by introducing the piece into a solvent for dissolution using an auxiliary cylinder according to the Disintegration Test defined in the Pharmacopoeia of Japan to thus determine the pH of the solvent which can dissolve the film. As the solvents for dissolution, there are used several kinds of Macvarin buffer solutions which are different from one another in pH values.

The base for coating the solid enteric pharmaceutical preparation is specifically prepared according to the following method. First of all, maleic anhydride and acetic anhydride are reacted with a water-soluble cellulose derivative in specific rates. Purified water is added to the reaction system to terminate the substitution reaction. After the completion of the reaction, an acid (a mineral acid such as hydrochloric acid or sulfuric acid) to the reaction system and then the reaction solution is poured into a large excess of water to thus sufficiently precipitate the coating base. Thereafter, the coating base is washed with purified water till the wash liquid does not exhibit an acidic pH any more. The resulting coating base can be dissolved in a solvent having a pH ranging from 3 to 4. The drying of the coating base may be carried out using, for instance, a fluidized bed dryer and may optionally be subjected to pulverization and classification.

The coating base prepared by the foregoing method is dissolved in an organic solvent such as acetone, methylene chloride/alcohol or alcohol/water, or dispersed in water after finely pulverizing into particles having a particle size of not more than 10 μm to thus give a coating liquid. The coating liquid may further comprise pharmaceutically acceptable additives such as a plasticizer, a coloring agent, a pigment and/or an antitack agent; and/or an existing coating base to control the release properties and the solubility of the coating base used in the present invention.

The coating treatment comprises spraying a drug with the coating liquid using a coating device and simultaneously drying the coating liquid applied to the drug to thus form a film. Examples of such coating devices are a fluidized bed coating device, a pan coating device and a flow-through rotational drum type coating device.

The film covering the solid enteric pharmaceutical preparation mainly comprises a coating base whose dissolution pH falls within the range of from 3 to 4. On the other hand, the conventional coating bases have a dissolution pH ranging from 5 to 7. For this reason, the film mainly comprising the coating base according to the present invention is apt to be easily dissolved in a more acidic solvent as compared with the films obtained from the conventional coating bases.

In the stomach, the coating film of the solid enteric pharmaceutical preparation is dissolved to some extent by the action of the gastric juice and the internal drug covered with the film begins to be released. The gastric juice is acidic and therefore, easily dissolve the film mainly comprising the coating base of the present invention. As described above, the film is dissolved in the gastric juice to some extent, the solid enteric pharmaceutical preparation already releases the drug contained therein at an instance when it reaches the small intestine and accordingly, it can completely release the drug till the preparation passes through the small intestine.

According to the solid enteric pharmaceutical preparation which is covered with the coating base of the present invention, the film is dissolved in the stomach by the action of the gastric juice and the preparation correspondingly begins to release the drug included therein. Therefore, the solid enteric pharmaceutical preparation permits complete release of the drug till it passes through the small intestine. For this reason, a largest possible amount of the drug included therein can be absorbed within the body and thus the preparation can ensure its high pharmacological action.

The present invention will hereinafter be described in more detail with reference to the following Examples, but the present invention is not limited to these specific Examples.

EXAMPLE 1

To a 5 liter biaxial kneader, there were introduced 700 g of hydroxypropylmethyl cellulose whose viscosity of a 2% by weight aqueous solution was 5.2 cP (methoxy group: 29.1% by weight; hydroxypropoxy groups: 8.9% by weight; HPMC available from Shin-Etsu Chemical Co., Ltd.) and 2100 g of acetic acid, followed by dissolving the cellulose at a temperature of 70° C. After the completion of the dissolution, 176 g of acetic anhydride and 193 g of maleic anhydride as esterifying agents were added to the resulting solution, then 278 g of sodium acetate as a catalyst was also added thereto and these reactants were reacted at a temperature ranging from 85° to 90° C. After 5 hours, the reaction solution was cooled and the reaction was terminated by the addition of 1180 g of purified water. The mixture obtained by adding 330 g of concentrated hydrochloric acid to the reaction system was poured into a large excess of purified water to thus separate out the reaction product. The product was washed with purified water till the wash liquid did not show acidity any more and then dried at 60° C. for 2 hours in a fluidized bed dryer to give hydroxypropylmethyl cellulose acetate maleate.

The degrees of substitution of the resulting hydroxypropylmethyl cellulose acetate maleate were found to be DS 1.90 (22.7%) for methoxy group, MS 0.24 (6.9%) for hydroxypropoxy group, DS 0.31 (5.1%) for acetyl group and DS 0.45 (17.2%) for maleyl group. In this respect, the terms "DS" and "MS" means "degree of substitution" and "molar substitution" respectively, both of which represent the number of each substituent introduced into the starting cellulose per glucose unit thereof.

The resulting cellulose acetate maleate was dissolved in a 1:1 methanol/methylene chloride mixed solvent and then the resulting solution was casted, on a glass plate, into a film having a thickness of 100 μm. The film was cut into pieces each having a size of 1 cm square and the piece was dissolved in a solvent according to the Disintegration Test defined in The Pharmacopoeia of Japan. More specifically, the film was added to several kinds of Macluvain buffer solutions having different pH values to determine the dissolution pH of the film and it was confirmed that the film was dissolved in a buffer solution having a pH of 3.5.

EXAMPLE 2

Hydroxypropylmethyl cellulose acetate maleate was prepared according to the same procedures used in Example 1 except that 285 g of acetic anhydride and 205 g of maleic anhydride were added.

The degrees of substitution of the resulting hydroxypropylmethyl cellulose acetate maleate were found to be DS 1.90 (22.1%) for methoxy group, MS 0.24 (6.7%) for hydroxypropoxy group, DS 0.48 (7.7%) for acetyl group and DS 0.45 (16.7%) for maleyl group.

A film was prepared from the resulting cellulose acetate maleate according to the same procedures used in Example 1 and then inspected for the dissolution pH. As a result, it was confirmed that the film was dissolved in a buffer solution having a pH of 4.0.

EXAMPLE 3

Hydroxypropylmethyl cellulose acetate maleate was prepared according to the same procedures used in Example 1 except that 170 g of acetic anhydride and 155 g of maleic anhydride were added.

The degrees of substitution of the resulting hydroxypropylmethyl cellulose acetate maleate were found to be DS 1.90 (23.5%) for methoxy group, MS 0.24 (7.2%) for hydroxypropoxy group, DS 0.31 (5.3%) for acetyl group and DS 0.36 (14.2%) for maleyl group.

A film was prepared from the resulting cellulose acetate maleate according to the same procedures used in Example 1 and then inspected for the dissolution pH. As a result, it was confirmed that the film was dissolved in a buffer solution having a pH of 3.9.

EXAMPLE 4

Hydroxypropylmethyl cellulose acetate maleate was prepared according to the same procedures used in Example 1 except that 182 g of acetic anhydride and 249 g of maleic anhydride were added.

The degrees of substitution of the resulting hydroxypropylmethyl cellulose acetate maleate were found to be DS 1.90 (21.5%) for methoxy group, MS 0.24 (6.6%) for hydroxypropoxy group, DS 0.31 (4.9%) for acetyl group and DS 0.59 (21.4%) for maleyl group.

A film was prepared from the resulting cellulose acetate maleate according to the same procedures used in Example 1 and then inspected for the dissolution pH. As a result, it was confirmed that the film was dissolved in a buffer solution having a pH of 3.1.

COMPARATIVE EXAMPLE 1

Hydroxypropylmethyl cellulose acetate maleate was prepared according to the same procedures used in Example 1 except that 320 g of acetic anhydride and 190 g of maleic anhydride were added.

The degrees of substitution of the resulting hydroxypropylmethyl cellulose acetate maleate were found to be DS 1.90 (22.0%) for methoxy group, MS 0.24 (6.7%) for hydroxypropoxy group, DS 0.62 (10.0%) for acetyl group and DS 0.40 (14.8%) for maleyl group.

A film was prepared from the resulting cellulose acetate maleate according to the same procedures used in Example 1 and then the pH of a solvent in which the film was soluble was determined. As a result, it was confirmed that the film was dissolved in a buffer solution having a pH of 4.4.

COMPARATIVE EXAMPLE 2

Hydroxypropylmethyl cellulose acetate maleate was prepared according to the same procedures used in Example 1 except that 190 g of acetic anhydride and 133 g of maleic anhydride were added.

The degrees of substitution of the resulting hydroxypropylmethyl cellulose acetate maleate were found to be DS 1.90 (23.8%) for methoxy group, MS 0.24 (7.3%) for hydroxypropoxy group, DS 0.37 (6.4%) for acetyl group and DS 0.30 (12.0%) for maleyl group.

A film was prepared from the resulting cellulose acetate maleate according to the same procedures used in Example 1 and then the pH of a solvent in which the film was soluble was determined. As a result, it was confirmed that the film was dissolved in a buffer solution having a pH of 4.3.

COMPARATIVE EXAMPLE 3

Hydroxypropylmethyl cellulose acetate succinate was prepared according to the same procedures used in Example 1 except that hydroxypropylmethyl cellulose whose viscosity of a 2% by weight aqueous solution was 8.9 cP (methoxy group: 28.7% by weight; hydroxypropoxy groups: 8.9% by weight; HPMC available from Shin-Etsu Chemical Co., Ltd.) and that 268 g of acetic anhydride was added and that 167 g of succinic anhydride was substituted for the maleic anhydride used in Example 1.

The degrees of substitution of the resulting hydroxypropylmethyl cellulose acetate succinate were found to be DS 1.87 (22.3%) for methoxy group, MS 0.24 (6.9%) for hydroxypropoxy group, DS 0.48 (8.0%) for acetyl group and DS 0.38 (14.6%) for succinate group.

A film was prepared from the resulting hydroxypropylmethyl cellulose acetate succinate according to the same procedures used in Example 1 and then inspected for the dissolution pH. As a result, it was confirmed that the film was dissolved in a buffer solution having a pH of 5.5.

What is claimed is:

1. A coating base for coating a solid enteric pharmaceutical preparation prepared by substituting at least one member selected from the group consisting of methyl cellulose, hydroxypropyl cellulose, hydroxypropylmethyl cellulose, and hydroxyethyl cellulose, with 0.25 to 0.5 acetyl group and 0.35 to 0.6 maleyl group per glucose ring of the cellulose, and having a dissolution pH ranging from 3 to 4.

2. The coating base according to claim 1 wherein the cellulose has a viscosity, as determined using a 2% by weight aqueous solution thereof, ranging from 3 to 10 cP.

\* \* \* \* \*